(12) United States Patent
Kelly et al.

(10) Patent No.: US 10,687,794 B2
(45) Date of Patent: Jun. 23, 2020

(54) DELIVERY CATHETER FOR IMPLANTABLE MEDICAL DEVICE

(71) Applicant: Medtronic, Inc., Minneapolis, MN (US)

(72) Inventors: Tomas K. Kelly, Co. Galway (IE); Paula McDonnell, Galway (IE); James M. Keaveney, Co. Galway (IE); Jeffrey Madden, County Mayo (IE)

(73) Assignee: Medtronic, Inc., Minneapolis, MN (US)

(\*) Notice: Subject to any disclaimer, the term of this patent is extended or adjusted under 35 U.S.C. 154(b) by 527 days.

(21) Appl. No.: 15/477,163

(22) Filed: Apr. 3, 2017

(65) Prior Publication Data
US 2018/0169375 A1 Jun. 21, 2018

Related U.S. Application Data

(60) Provisional application No. 62/436,700, filed on Dec. 20, 2016.

(51) Int. Cl.
*A61B 17/00* (2006.01)
*A61B 17/34* (2006.01)
*A61B 5/02* (2006.01)

(52) U.S. Cl.
CPC .... *A61B 17/00234* (2013.01); *A61B 17/3468* (2013.01); *A61B 5/02* (2013.01); *A61B 2017/00022* (2013.01); *A61B 2560/066* (2013.01)

(58) Field of Classification Search
CPC . A61B 17/00234; A61B 17/3468; A61B 5/02; A61B 2017/00022; A61B 2560/066
See application file for complete search history.

(56) References Cited

U.S. PATENT DOCUMENTS

| 5,372,600 A | 12/1994 | Beyar et al. |
| 6,562,064 B1 | 5/2003 | deBeer |
| 8,021,307 B2 | 9/2011 | White et al. |
| 8,355,777 B2 | 1/2013 | White et al. |
| 8,727,996 B2 | 5/2014 | Allan et al. |
| 8,864,676 B2 | 10/2014 | Beasley et al. |
| 2006/0200030 A1* | 9/2006 | White ............... A61B 5/0215 600/486 |

(Continued)

OTHER PUBLICATIONS

U.S. Appl. No. 15/846,797, filed by Tomas K. Kelly et al., filed Dec. 19, 2017.

*Primary Examiner* — Patrick Fernandes

(57) ABSTRACT

A kit for implantation of an implantable medical device (IMD) comprises an elongated outer shaft, a tether, and an elongated inner shaft. The IMD comprises a fixation element comprising a looped portion. The outer shaft is sized to traverse a vasculature of the patient and defines a longitudinal lumen and a port in fluid communication with the lumen and located proximal a distal end of the outer shaft. A first portion of the tether is configured to pass through the lumen. A second portion of the tether is configured to exit the lumen through the port and pass through the looped portion of the fixation element of the IMD outside of the outer shaft. A third portion of the tether defines a looped portion of the tether. A portion of the inner shaft is configured to pass through the lumen and to pass through the looped portion of the tether.

19 Claims, 13 Drawing Sheets

(56) References Cited

U.S. PATENT DOCUMENTS

| | | | |
|---|---|---|---|
| 2013/0253309 A1* | 9/2013 | Allan | A61B 6/00 |
| | | | 600/424 |
| 2013/0253347 A1 | 9/2013 | Griswold et al. | |
| 2016/0287334 A1* | 10/2016 | Grant | A61B 18/02 |
| 2016/0310703 A1 | 10/2016 | Drake et al. | |

* cited by examiner

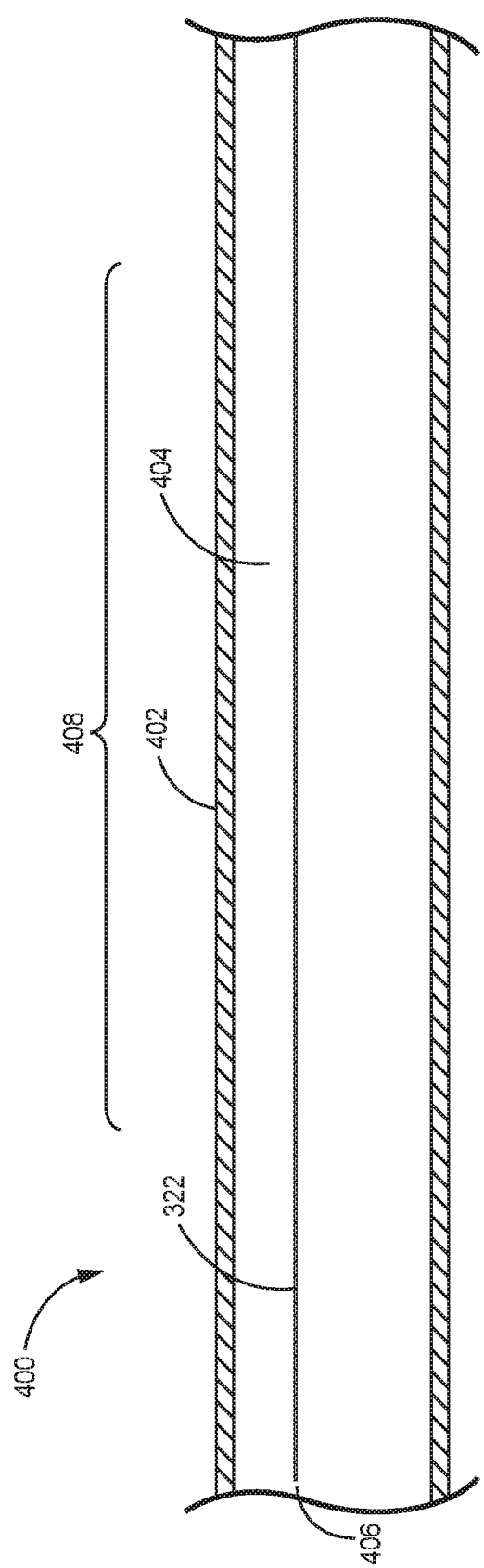

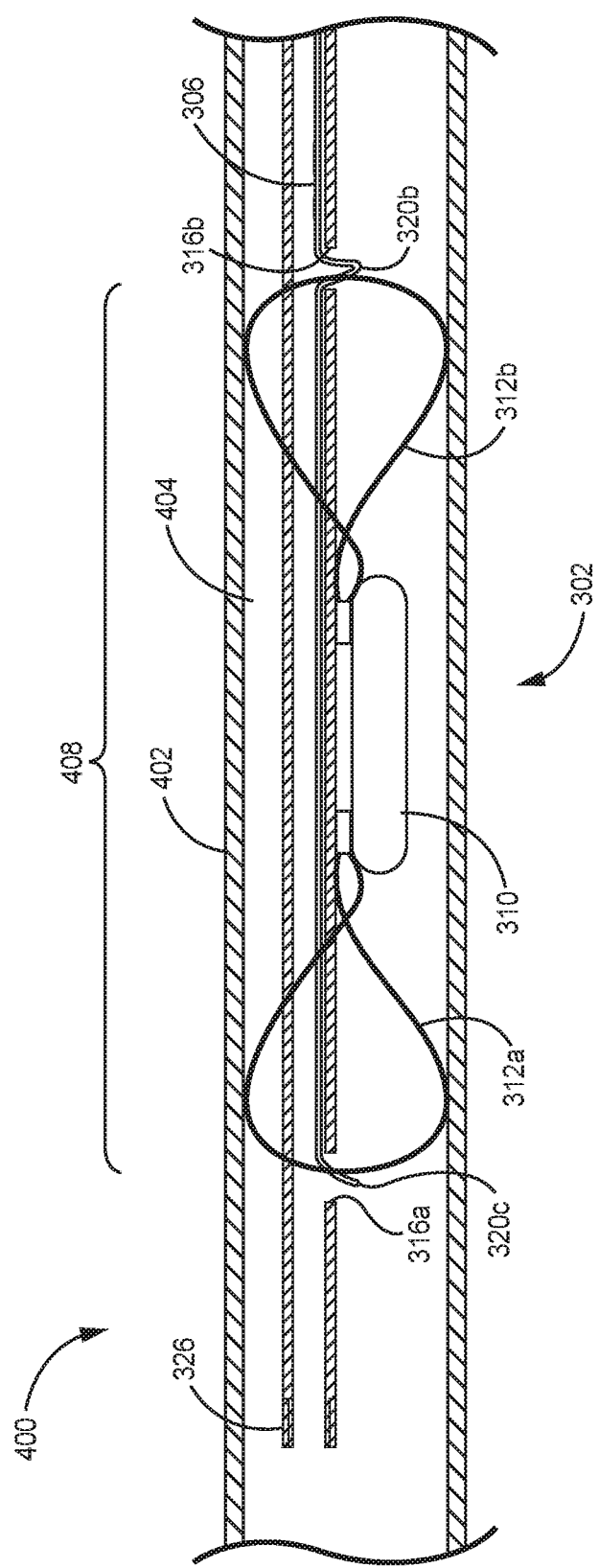

DELIVERY CATHETER FOR IMPLANTABLE MEDICAL DEVICE

This application claims the benefit of U.S. Provisional Application No. 62/436,700, filed Dec. 20, 2016, the entire content of which is hereby incorporated by reference.

TECHNICAL FIELD

The disclosure relates to medical devices and, more particularly, devices for delivering implantable medical devices.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads for placing electrodes or sensors at target locations, or may be leadless. Such devices may also have the ability to wirelessly transmit data either to another device implanted in the patient or to another device located externally of the patient, or both. Although implantation of some devices requires a surgical procedure, other devices may be small enough to be delivered and placed at an intended implant location in a relatively noninvasive manner, such as by a percutaneous delivery catheter.

By way of illustrative example, implantable miniature sensors have been proposed and used in blood vessels to measure directly the diastolic, systolic and mean blood pressures, as well as body temperature and cardiac output. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, particularly patients suffering from chronic heart failure, may benefit from the use of implantable sensors adapted to monitor blood pressures. Promising indications have been reported for using such implantable sensors.

SUMMARY

The disclosure describes delivery catheters, systems and associated techniques, structures and assemblies for delivery of implantable devices within the body of the patient. In an aspect, delivery catheters are described that may include provide improved kink resistance and a reduced profile (and thus improved maneuverability) and more accurate deployment than other catheter designs including an outer sheath and/or a balloon for retaining the sensor in place and/or for deploying the sensor. The described delivery catheters may also more reliably secure an implantable medical device, including fixation means, to the delivery catheter, which may reduce the risk of contact damage from the fixation means contacting the walls of the vasculature before intended deployment of the implantable medical device. Additionally, the delivery catheters may provide ease of deployment compared to other designs.

In one example, a kit for intravascular implantation of an implantable medical device (IMD) within a patient comprises an elongated outer shaft, a tether, and an elongated inner shaft. The IMD comprises a fixation element comprising a looped portion. The outer shaft defines a longitudinal lumen and a port in fluid communication with the lumen. The port is located proximal a distal end of the shaft. The outer shaft is sized to traverse a vasculature of the patient. At least first portion of the tether is configured to pass through the lumen of the outer shaft. At least a second portion of the tether is configured to exit the lumen through the port and pass through the looped portion of the fixation element of the implantable medical device outside of the elongated outer shaft. At least a third portion of the tether defines a looped portion of the tether. At least a portion of the inner shaft is configured to pass through the lumen of the outer shaft and to pass through the looped portion of the tether to prevent removal of the tether from the outer shaft when the portion of the inner shaft passes through the looped portion of the tether.

In another example, a method for intravascular implantation of an IMD comprises positioning a distal end of an assembly at a target vascular location for implantation of the IMD, retracting an elongated inner shaft relative to an elongated outer shaft, and retracting a tether relative to the outer shaft. The assembly comprises the outer shaft, the IMD, a tether, and the inner shaft. The outer shaft defines a longitudinal lumen and a port in fluid communication with the lumen. The port is located proximal a distal end of the outer shaft. The outer shaft is sized to traverse a vasculature of the patient. The IMD comprises a fixation element comprising a looped portion. At least first portion of the tether is configured to pass through the lumen of the outer shaft. At least a second portion of the tether is configured to exit the lumen through the port and pass through the looped portion of the fixation element of the implantable medical device outside of the elongated outer shaft. At least a third portion of the tether defines a looped portion of the tether. At least a portion of the inner shaft is configured to pass through the lumen of the outer shaft and to pass through the looped portion of the tether to prevent removal of the tether from the outer shaft when the portion of the inner shaft passes through the looped portion of the tether.

In another example, a kit for intravascular implantation of an IMD within a patient comprises an elongated outer shaft, the IMD, a tether, and an elongated inner shaft. The elongated outer shaft defines a longitudinal lumen and a port in fluid communication with the lumen. The port is located proximal a distal end of the outer shaft. The outer shaft is sized to traverse a vasculature of the patient. The IMD comprises a fixation element comprising a looped portion. At least first portion of the tether is configured to pass through the lumen of the outer shaft. At least a second portion of the tether is configured to exit the lumen through the port and pass through the looped portion of the fixation element of the implantable medical device outside of the elongated outer shaft. At least a third portion of the tether defines a looped portion of the tether. At least a portion of the inner shaft is configured to pass through the lumen of the outer shaft and to pass through the looped portion of the tether to prevent removal of the tether from the outer shaft when the portion of the inner shaft passes through the looped portion of the tether.

In a further example, a kit for intravascular implantation of an IMD within a patient comprises an elongated outer shaft, a tether, and an elongated inner shaft. The IMD comprises a fixation element comprising first and second looped portions. The elongated outer shaft defines a longitudinal lumen, a proximal port in fluid communication with the lumen, and a distal port in fluid communication with the lumen. Each of the proximal port and the distal port is located proximal a distal end of the outer shaft and defined on a side wall of the outer shaft. The outer shaft is sized to traverse a vasculature of the patient. At least first portion of the tether is configured to pass through the lumen of the outer shaft. At least a second portion of the tether is configured to exit the lumen through the proximal port and pass through the first looped portion of the fixation element of the IMD outside of the elongated outer shaft. At least a third portion of the tether is configured to exit the lumen through the distal port and pass through the second looped portion of the fixation element of the IMD outside of the elongated outer shaft. At least a fourth portion of the tether defines a looped portion of the tether. At least a portion of the inner shaft is configured to pass through the lumen of the outer shaft and to pass through the looped portion of the tether to prevent removal of the tether from the outer shaft when the portion of the inner shaft passes through the looped portion of the tether.

In an additional example, a kit for intravascular implantation of an IMD within a patient comprises an elongated outer shaft, a tether, and an elongated inner shaft. The IMD comprises a fixation element comprising first and second looped portions. The elongated outer shaft defines a longitudinal lumen, a proximal port in fluid communication with the lumen, and a distal port in fluid communication with the lumen. Each of the proximal port and the distal port is located proximal a distal end of the outer shaft and defined on a side wall of the outer shaft. The outer shaft is sized to traverse a vasculature of the patient. The proximal port is circumferentially spaced approximately 180 degrees about the outer shaft from the distal port. A distal portion of the outer shaft comprises a radiopaque marker. At least first portion of the tether is configured to pass through the lumen of the outer shaft. At least a second portion of the tether is configured to exit the lumen through the proximal port and pass through the first looped portion of the fixation element of the IMD outside of the elongated outer shaft. At least a third portion of the tether is configured to exit the lumen through the distal port and pass through the second looped portion of the fixation element of the IMD outside of the elongated outer shaft. At least a fourth portion of the tether defines a looped portion of the tether. At least a portion of the inner shaft is configured to pass through the lumen of the outer shaft and to pass through the looped portion of the tether to prevent removal of the tether from the outer shaft when the portion of the inner shaft passes through the looped portion of the tether.

It should be understood that although the disclosure is described principally in the context of delivering a sensor in a blood vessel, the disclosure is not limited to use in that context. The principles of the disclosure may be used to deliver implantable sensors assemblies adapted to measure and monitor any of a variety of physiological parameters or to medical devices for delivery of therapy.

The details of one or more examples of the invention are set forth in the accompanying drawings and the description below. Other features, objects, and advantages of the invention will be apparent from the description and drawings, and from the claims.

BRIEF DESCRIPTION OF THE DRAWINGS

FIGS. 4A-4E are partial, schematic views of the example kit of FIGS. 3A-3C in various stages of use at an example treatment site within a vasculature of a patient.

DETAILED DESCRIPTION

The present disclosure describes catheter-based systems for delivering miniaturized devices that sense various physiological parameters of a patient such as blood pressure. Such miniaturized devices include implantable medical devices that may comprise a hermetic housing that contains a battery and electronics, and a fixation assembly. The delivery catheter is provided to interface with the sensor device for accurately and efficiently delivering the sensor device. The design of the delivery catheter provides flexibility, thus providing efficient delivery through the vascular structure which includes tortuous pathways defined by the blood vessels of the patient. The design of the delivery catheter also provides accurate delivery of the sensor device at the target site compared to other designs requiring retraction of an outer sheath and/or a balloon with respect to the sensor device, which may lead to undesired movement of the sensor device during or after deployment.

This disclosure will describe delivery assemblies in the context of delivering a pressure sensing miniaturized device. However, it should be understood that the delivery devices may be used in conjunction with other types of miniaturized devices such as temperature sensors, cardiac output sensors or therapy delivery devices such as pacemakers and drug delivery devices.

In various examples, a delivery assembly formed in accordance with this disclosure may provide one or more advantages. For example, the delivery assemblies may have reduced dimensions and be composed of more desirable (e.g. flexible) materials for tracking through vasculature compared to delivery systems requiring an outer sheath to secure an IMD to a delivery catheter. For example, such dimensions and composition may result in greater kink resistance. This may be particularly important, for example, for delivery to the pulmonary artery. Tracking from the right ventricle, through the pulmonary valve, and into the pulmonary artery (an approximately 90 degree turn), may result in unpredictable kinking which may be reduced or eliminated by the described delivery assemblies.

Additionally, the delivery catheters described herein may provide ease of deployment compared to other designs. For example, the described delivery assemblies may result in more accurate deployment. Other assemblies may require that an IMD be pushed out of an outer sheath and that a balloon be retracted proximally past the IMD, which may result in distal migration of the IMD. The delivery assemblies describe herein may eliminate the need for an outer sheath and/or a balloon, thus eliminating this potential migration.

Further, the described delivery assemblies may more reliably secure the IMD, including fixation means, to the delivery device, which may reduce the risk of contact damage from the fixation means contacting the walls of the vasculature before intended deployment of the IMD.

Figure 1A:
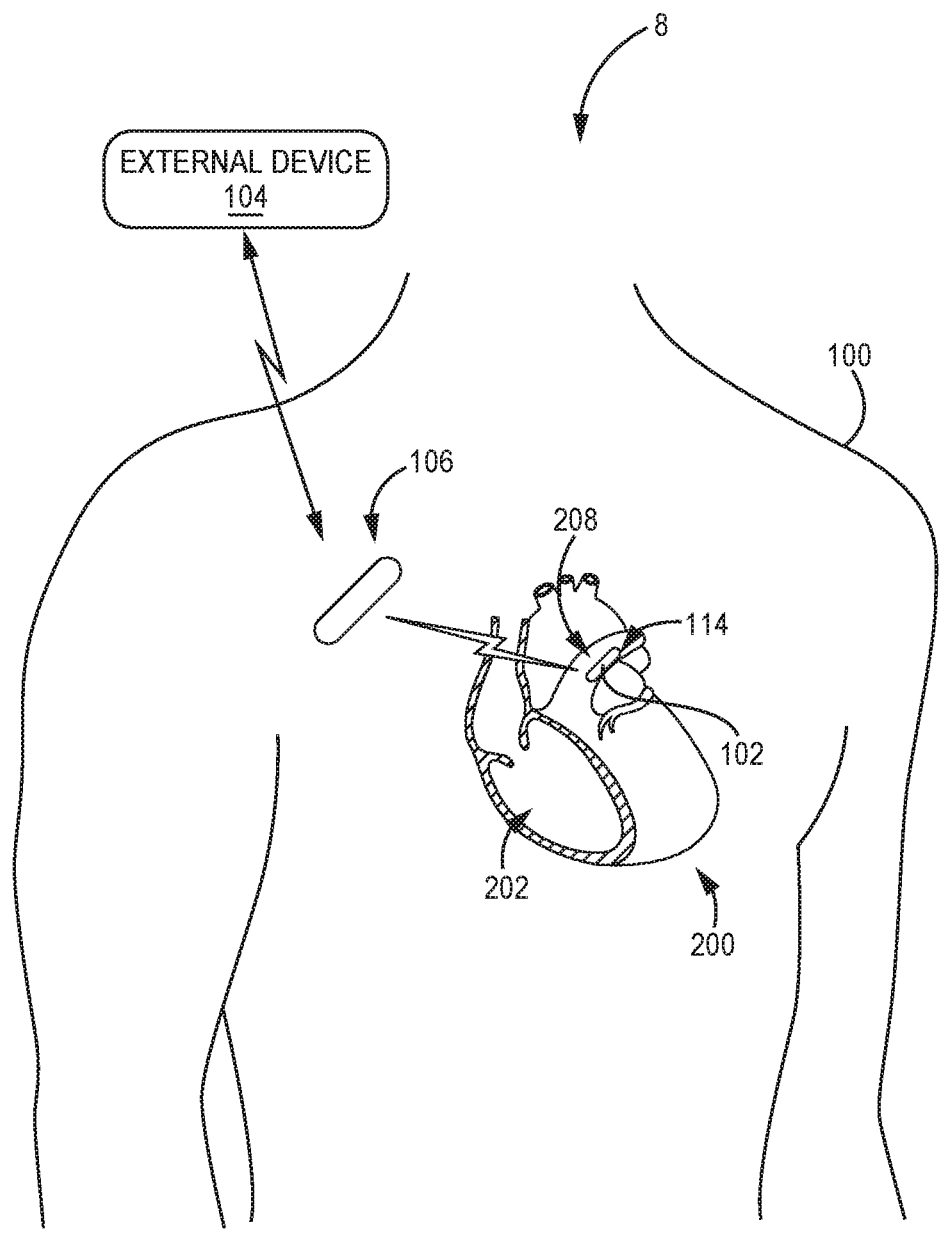
FIG. 1A illustrates, diagrammatically, an example of a patient with implanted medical devices.

FIG. 1A illustrates, diagrammatically, an example of a patient 100 with implanted medical devices including a sensor assembly 114 implanted, for example, in the patient's left pulmonary artery 208 through which blood flows from heart 200 to the lungs, and another device, such as an implantable or insertable cardiac monitor, an implantable hub device or the like, referred to as IMD 106. For purposes of this description, knowledge of cardiovascular anatomy is presumed and details are omitted except to the extent necessary or desirable to explain the context of the invention.

Medical device system 8 is an example of a medical device system configured to monitor cardiovascular parameters and/or other physiological parameters of patient 100. In the illustrated example, medical device system 8 includes an implantable medical device (IMD) 106, which may comprise an implantable or insertable cardiac monitor or an implantable hub device, in communication with external device 104. Medical device system 8 also includes implantable sensor assembly 114, which comprises sensing device 102. As shown in FIG. 1A, implantable sensor assembly 114 may be implanted within pulmonary artery 208 of heart 200.

In the illustrated example, IMD 106 comprises an insertable cardiac monitor (ICM) configured to sense and record cardiac electrogram (EGM) signals from a position outside of heart 200, and will be referred to as ICM 106 hereafter. In some examples, ICM 106 includes or is coupled to one or more additional sensors, such as accelerometers, that generate one or more signals that vary based on patient motion, posture, blood flow, or respiration. ICM 106 may monitor a physiological parameter such as posture, heart rate, activity level, and/or respiration rate, and may do so at times when the one or more additional sensors, such as sensing device 102, is measuring a patient parameter such as cardiovascular pressure or any other suitable patient parameter. ICM 106 may be implanted outside of the thoracic cavity of patient 100, e.g., subcutaneously or submuscularly, such as at the pectoral location illustrated in FIG. 1A. In some examples, ICM 106 may take the form of a Reveal LINQ™ ICM, available from Medtronic plc, of Dublin, Ireland.

Sensing device 102 may be implanted within a pulmonary artery 208 of patient 100 and may include sensing circuitry configured to measure a parameter of patient 100. For example, sending device 102 may include pressure sensing circuitry configured to measure cardiovascular pressure of patient 100. Each of sensing device 102 and ICM 106 may include a timer and processing circuitry configured to determine a time of day based on the timer value. If sensing device 102 determines that the current time is within a predetermined window that may be stored in memory of sensing device 102, sensing device 102 may measure a parameter of patient 100, which may be contemporaneously or later transmitted to ICM 106. In some examples, sensing device 102 may include wireless communication circuitry configured to receive a trigger signal from ICM 106, e.g., instead of or in addition to the timer and processing circuitry to independently determine when to make a measurement of a patient parameter. In such examples, processing circuitry of sensing device 102 may be configured to control the sensing circuitry of sensing device 102 to measure the patient parameter of patient 100 in response to receiving the trigger signal. In this manner, ICM 106 may dictate the times at which sensing device 102 measures a patient parameter, and sensing device 102 may enter a low-power mode such as sleep mode until the wireless communication circuitry of sensing device 102 receives a trigger signal.

ICM 106 may transmit data, including, for example, posture data and/or other physiological parameter data acquired by ICM 106, to external device 104. ICM 106 also may transmit measurements received from sensing device 102 to external device 104. For example, ICM 106 may transmit data related to cardiovascular pressure, posture, heart rate, activity level, respiration rate, and/or other physiological parameters to external device 104. External device 104 may be a computing device configured for use in settings such as a home, clinic, or hospital, and may further be configured to communicate with ICM 106 via wireless telemetry. For example, external device 104 may be coupled to a remote patient monitoring system, such as Carelink®, available from Medtronic plc, of Dublin, Ireland. External device 104 may, in some examples, comprise a programmer, an external monitor, or a consumer device such as a smart phone.

External device 104 may be used to program commands or operating parameters into ICM 106 for controlling its functioning, e.g., when configured as a programmer for ICM 106. External device 104 may be used to interrogate ICM 106 to retrieve data, including device operational data as well as physiological data accumulated in the memory of ICM 106. The accumulated physiological data may include, for example, cardiovascular pressure generally, such as one or more of a systolic pressure, a diastolic pressure, and a mean pulmonary artery pressure, or medians of such pressures, and/or other forms of physiological data. In some examples, the interrogation may be automatic, e.g., according to a schedule. In other examples, the interrogation may occur in response to a remote or local user command. Programmers, external monitors, and consumer devices are examples of external devices 104 that may be used to interrogate ICM 106.

Examples of wireless communication techniques used by ICM 106 and external device 104 include radiofrequency (RF) telemetry, which may be an RF link established via an antenna according to Bluetooth, WiFi, or medical implant communication service (MICS), or transconductence communication (TCC), which may occur via electrodes of ICM 106. Examples of wireless communication techniques used by ICM 106 and sensing device 102 may also include RF telemetry or TCC. In one example, ICM 106 and sensing device 102 communicate via TCC, and ICM 106 and external device 104 communicate via RF telemetry.

Medical device system 8 is an example of a medical device system configured to monitor a cardiovascular parameters of patient 100 and may additionally or alternatively include other medical devices. For example, some additional or alternative medical devices that may be used include external devices configured to monitor posture, heart rate, activity level, respiration rate, and/or other physiological parameters. Although not illustrated in the example of FIG. 1A, medical device system 8 may include one or more implanted or external medical devices in addition to or instead of ICM 106 and sensing device 102. For example, a medical device system may include a vascular ICD or pacemaker (e.g., IMD 16 illustrated in FIG. 1B), an extravascular ICD, or an intracardiac pacemaker. One or more such devices may generate physiological signals, and may include processing circuitry configured to perform, in whole or in part, the techniques described herein for monitoring cardiovascular pressure. In some examples, the implanted devices may communicate with each other and/or with external device 104.

For sake of clarity, sensor assembly 114 is shown without a fixation assembly in FIG. 1A. A suitable fixation assembly configured to secure sensor assembly 114 within pulmonary artery 208 will be discussed below with respect to FIGS. 2A and 2B. The sensor device 102 of the sensor assembly 114 also may communicate wirelessly with the external device 104, either directly or via device 106, to provide in vivo data for selected physiological parameters to an external site to inform clinicians of the patient's status. Although not depicted, sensor device 102 may include wireless communication capabilities, such as low frequency or radiofrequency (RF) telemetry, transconductance communication (TCC), or other wireless communication techniques that allow sensor device 102 to communicate with device 106, external device 104, or another device.

Sensor assembly 114 may be a leadless assembly, e.g., need not be physically coupled to an IMD or other device via a lead, and need not otherwise be coupled to any leads. Although illustrated as being located in the pulmonary artery 208, in some examples, sensory assembly 114 may be located in the right ventricle 202, aorta, and/or other locations within the pulmonary and systemic circulatory systems of patient 100. Sensor assembly 114 may be affixed to the wall of the pulmonary artery 208 or, as another example, the wall of the right ventricle 202. In some examples, pulmonary artery 208 of heart 200 may comprise a left pulmonary artery, whereas in other examples, pulmonary artery 208 may comprise a right pulmonary artery.

Figure 1B:
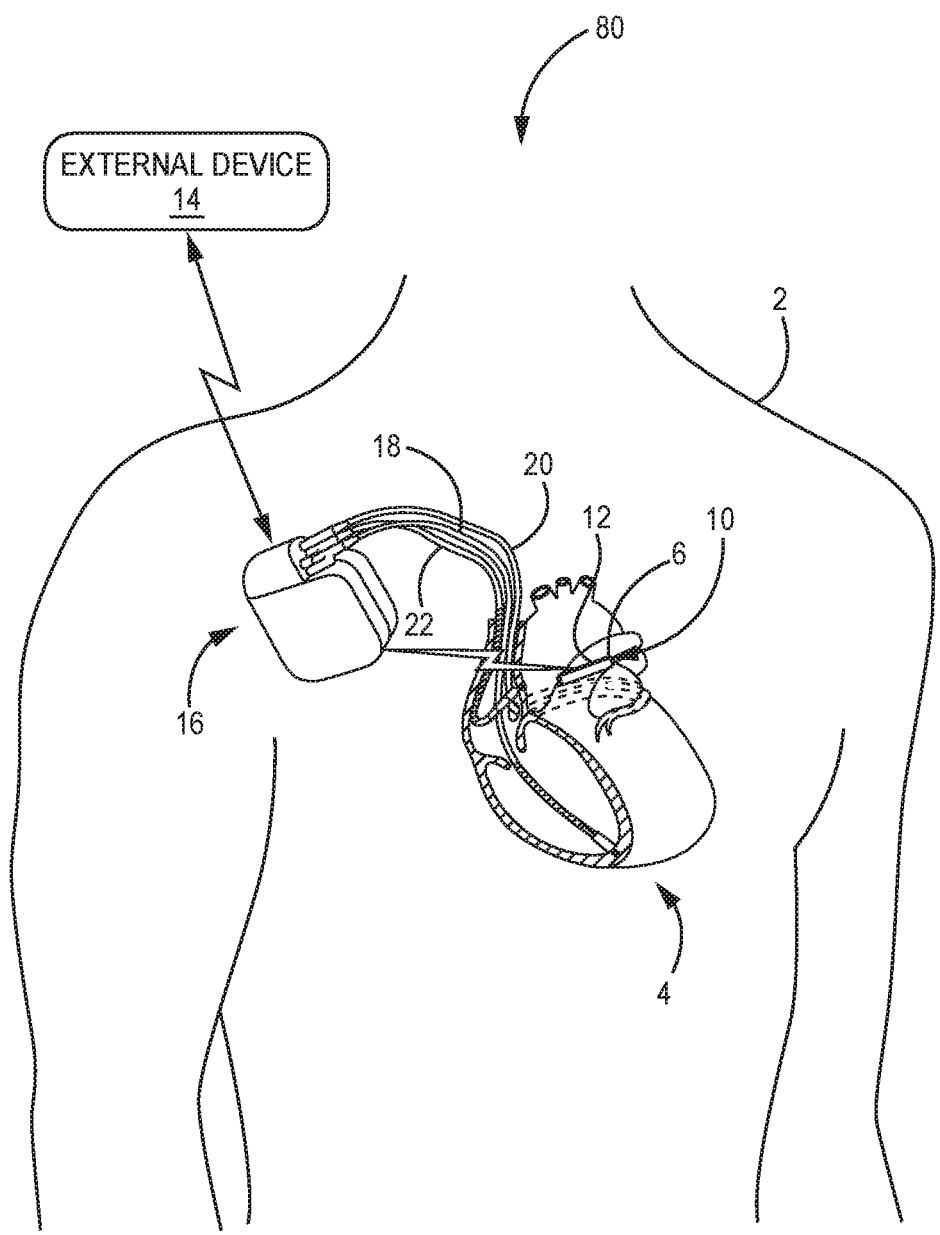
FIG. 1B illustrates, diagrammatically, another example of a patient with implanted medical devices.

FIG. 1B illustrates, diagrammatically, an example of a patient 2 with implanted medical devices including a sensor assembly 10 implanted, for example, in the patient's left pulmonary artery 12 through which blood flows from heart 4 to the lungs, and another device, such as a pacemaker, defibrillator or the like, referred to as IMD 16. For purposes of this description, knowledge of cardiovascular anatomy is presumed and details are omitted except to the extent necessary or desirable to explain the context of the invention.

Medical device system 80, including implantable sensor assembly 10 and IMD 16, is another example of a medical device system configured to implement to monitor cardiovascular parameters. The implantable pressure sensing device 6 of assembly 10, IMD 116, and external device 14 in FIG. 1B may provide substantially similar functionality as the like numbered devices described above with respect to FIG. 1A.

In some examples, IMD 16 may include one or more leads 18, 20, 22 that carry electrodes that are placed in electrical contact with selected portions of the cardiac anatomy in order to perform the functions of IMD 16 as is well known to those skilled in the art. For example, IMD 16 may be configured to sense and record cardiac EGM signals via the electrodes on leads 18, 20, 22. IMD 16 may also be configured to deliver therapeutic signals, such as pacing pulses, cardioversion shocks, or defibrillation shocks, to heart 4 via the electrodes. In the illustrated example, IMD 16 may be a pacemaker, cardioverter, and/or defibrillator.

In some examples, this disclosure may refer to IMD 16, particularly with respect to its functionality as part of a medical device system that monitors cardiovascular pressure and other physiological parameters of a patient 2, as an implantable monitoring device or implantable hub device. In some examples, IMD 16 includes or is coupled to one or more additional sensors, such as accelerometers, that generate one or more signals that vary based on patient motion and/or posture, blood flow, or respiration. IMD 16 may monitor posture of patient 2 at or near the times when implantable pressure sensing device 6 is measuring a cardiovascular parameter such as, for example, cardiovascular pressure.

IMD 16 also may have wireless capability to receive and transmit signals relating to the operation of the device. IMD 16 may communicate wirelessly to an external device, such as external device 14, and/or to another implanted device such as implantable sensing device 6 of the sensor assembly 10, e.g., as described above with respect to IMD 106, external device 104, and sensing device 102 of FIG. 1A. In some examples, an implantable sensing device 6 may communicate wirelessly and directly with an external device 14, rather than communicating with the external device 14 through the IMD 16.

Medical device system 80 is an example of a medical device system configured to monitor a cardiovascular parameter of patient 2 and may perform similar functions to the medical device system 8 of FIG. 1A described above.

For sake of clarity, sensor assembly 6 is shown without a fixation assembly in FIG. 1B. A suitable fixation assembly configured to secure sensor assembly 6 within pulmonary artery 12 will be discussed below with respect to FIGS. 2A and 2B. The sensor device 6 of the sensor assembly 10 also may communicate wirelessly with the external 14, either directly or via device 16, to provide in vivo data for selected physiological parameters to an external site to inform clinicians of the patient's status. Although not depicted, sensor device 6 may include wireless communication capabilities, such as low frequency or radiofrequency (RF) telemetry, transconductance communication (TCC), or other wireless communication techniques that allow sensor device 6 to communicate with device 16, external device 14, or another device.

Sensor assembly 10 may be a leadless assembly, e.g., need not be physically coupled to an IMD or other device via a lead, and need not otherwise be coupled to any leads. Although illustrated as being located in the pulmonary artery 12, in some examples, sensory assembly 10 may be located in the right ventricle, aorta, and/or other locations within the pulmonary and systemic circulatory systems of patient 2. Sensor assembly 10 may be affixed to the wall of the pulmonary artery 12 or, as another example, the wall of the right ventricle. In some examples, pulmonary artery 12 of heart 4 may comprise a left pulmonary artery, whereas in other examples, pulmonary artery 12 may comprise a right pulmonary artery.

Figure 2A:
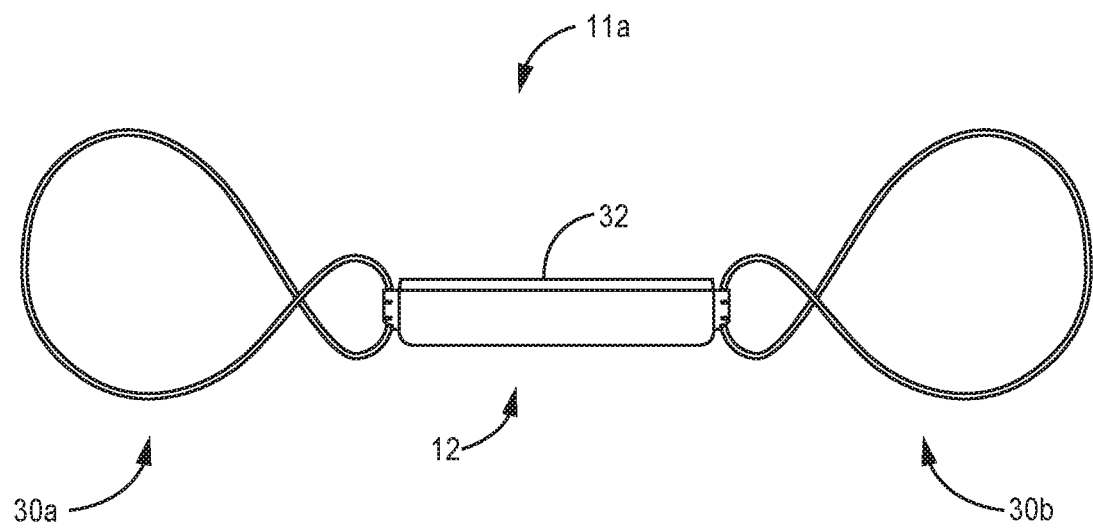
FIGS. 2A and 2B are side profile views of respective example configurations of a sensor assembly.
Figure 2B:
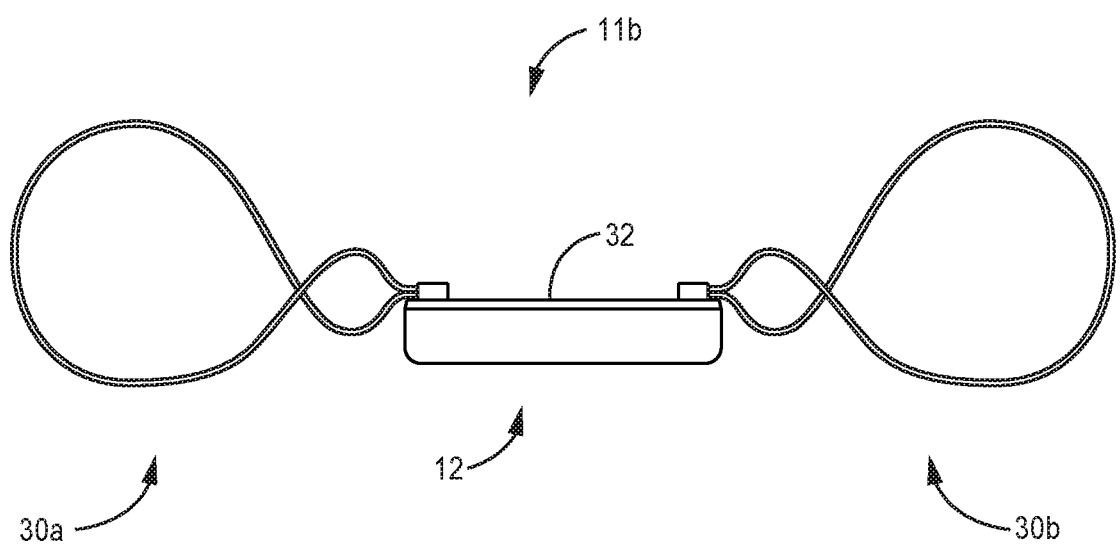

FIGS. 2A and 2B are side profile views of example configurations of a sensor assembly; sensor assembly 11a and sensor assembly 11b (collectively "sensor assembly 10"). The sensor assembly 10 includes a sensor 12 coupled to fixation members 30a, 30b (collectively "fixation assembly 30"). The fixation assembly 30 and sensor 12 are arranged to enable the sensor assembly 10 to be provided in a delivery configuration that enables it to be navigated to an implant location where it can be deployed into the deployment configuration. As described in this disclosure, it should be understood that the delivery configuration defines a pitch, width or diameter that is narrower, in relation to the deployment configuration, along a common plane. Upon release, the fixation assembly expands into the deployment configuration so as to be in physical contact with the wall of the blood vessel to maintain the positional integrity of sensor 12.

In one example, the fixation assembly will engage the interior wall of the vessel defining the blood flow lumen. The sensor 12 is attached to the fixation assembly 30 in a manner such that the sensing element 32 of the sensor 12 is spaced from the wall of the vascular lumen to minimize adverse obstruction to blood flow through the lumen and to position the sensing element 32 of the sensor 12 to be fully exposed to the blood in the vessel, without obstruction from the housing of the sensor 12 or the vessel wall.

Figure 3A:
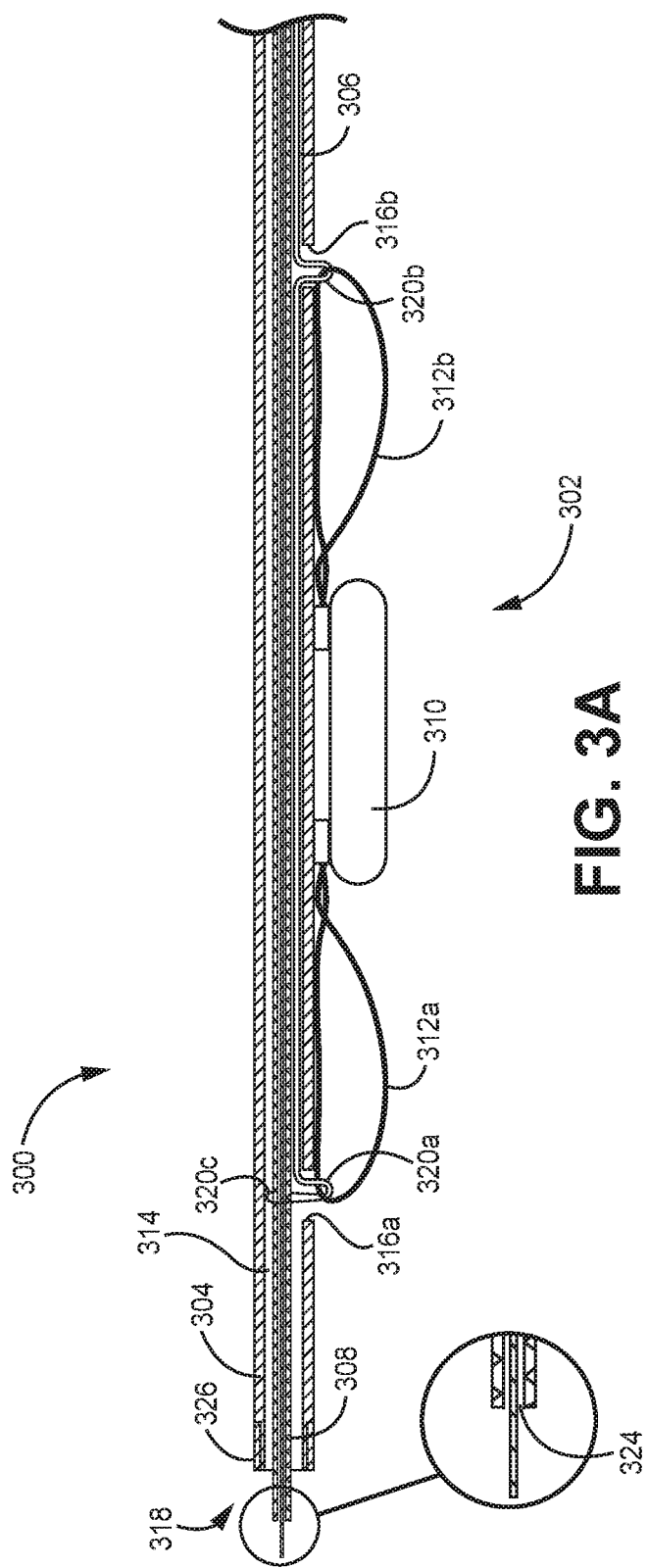
FIGS. 3A, 3B, and 3C illustrate side cross-sectional, side profile, and partially expanded side profile views of a portion of an example kit for intravascular implantation of an implantable medical device (IMD) within a patient.
Figure 3B:
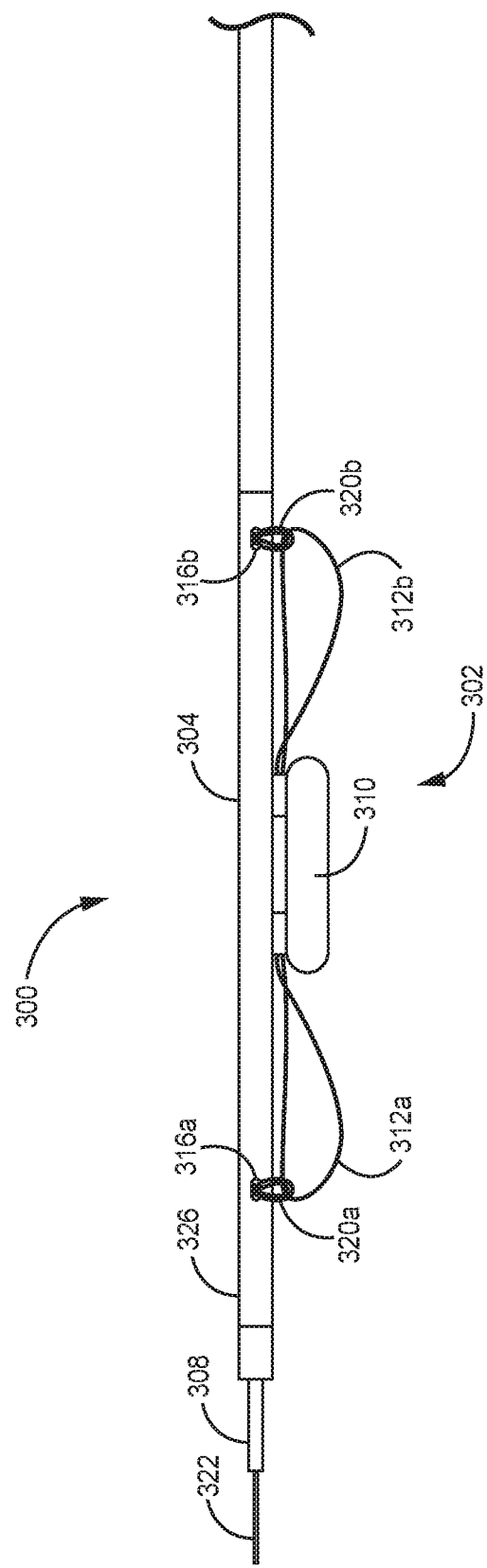
Figure 3C:
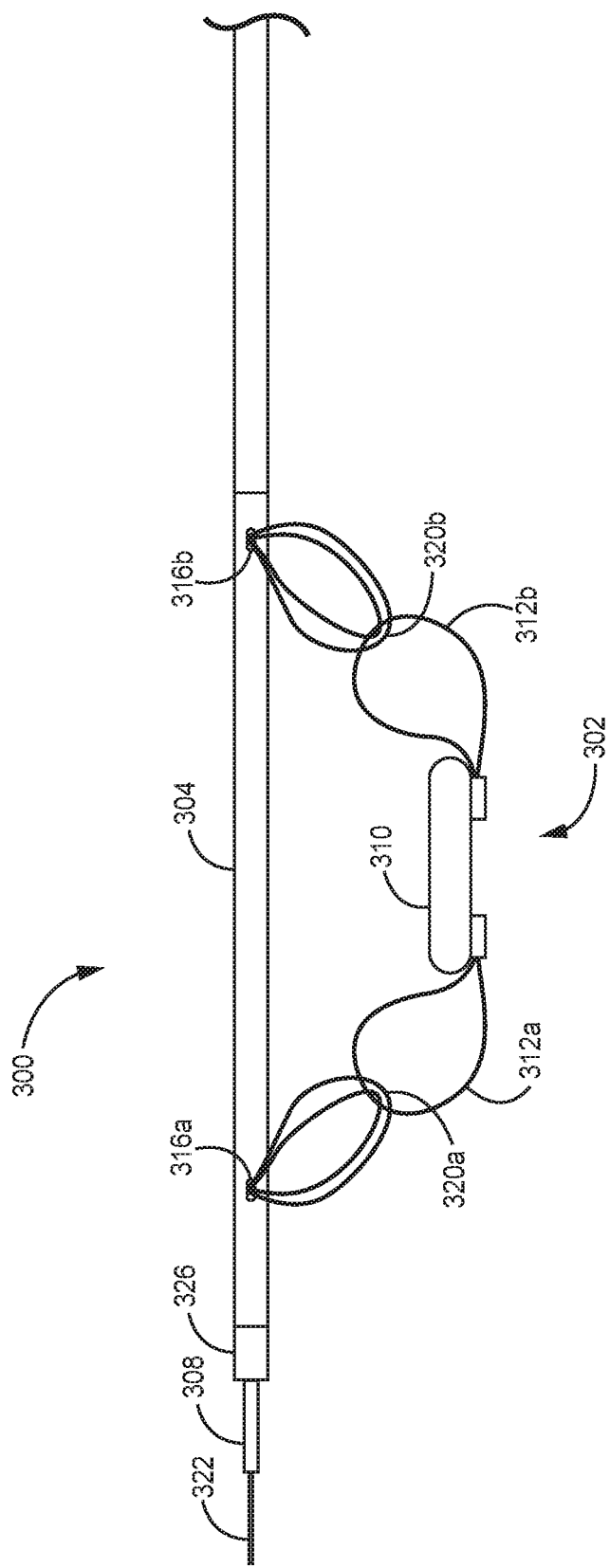

FIGS. 3A, 3B, and 3C illustrate side cross-sectional, side profile, and partially expanded side profile views of a portion of an example of a kit 300 for intravascular implantation of an implantable medical device (IMD) 302 within a patient. The IMD 302 may be, for example, a sensor assembly, such as the sensor assemblies 114, 10, 11a, and 11b of FIGS. 1A-2B. In some examples, the IMD 302 may comprise a sensor, such as a sensor configured to measure blood pressure.

The kit 300 may include an elongated outer shaft 304, a tether 306, and an elongated inner shaft 308. In some examples, the kit 300 may further include the IMD 302.

The IMD 302 may include a housing 310 and a fixation assembly 312. The fixation assembly 312 may include, for example, two looped portions 312a and 312b which may each form a loop. The looped portions 312a and 312b may comprise nitinol or any other suitable material and may be expandable such that they are configured to expand to engage with walls of a vasculature when released within the vasculature.

The outer shaft 304 may be sized to traverse a vasculature of the patient and may define a longitudinal lumen 314, one or more ports 316 in fluid communication with the lumen 314 and a distal end 318. The ports 316a and 316b (collectively "ports 316") may be located proximal to the distal end 318 of the outer shaft 304. The ports 316 may include a proximal port 316b and a distal port 316a, each defined on a side wall of the outer shaft 304.

The tether 306 may comprise a polyester suture, nylon monofilament, and/or another similar material. The tether may have an outer diameter of approximately 0.15-0.2 mm. As shown, a portion of the tether 306 may be configured to pass through the lumen 314 of the outer shaft 304. In some examples, a portion 320a of the tether 306 is configured to exit the lumen 314 through the port 316a and pass through the looped portion 312a of the fixation assembly 312 of the IMD 302 outside of the outer shaft 304. In some examples, a portion 320b of the tether 306 is configured to exit the lumen 314 through the port 316b and pass through the looped portion 312b of the fixation element 312 of the IMD 302 outside of the outer shaft 304. A portion of the tether 306 may define a looped portion 320c of the tether 306.

The inner shaft 308 may be a braided polyamide shaft. As shown, portion of the inner shaft 308 may be configured to pass through the lumen 314 of the outer shaft 304 and to pass through the looped portion 320c of the tether 306 to prevent removal of the tether 306 from the outer shaft 304 when the portion of the inner shaft 308 passes through the looped portion 320c of the tether 306. In some examples, the inner shaft 308 may, but does not necessarily, run the full length of the outer shaft 304. In some examples, the kit 300 may include a guidewire 322 and the inner shaft 308 may define a guidewire lumen 324 configured for passage of the guidewire 322.

In some examples, a distal portion of the outer shaft 304 may include a marker band 326, which may, comprise, for example, a gold radiopaque ribbon section, a barium sulphate filled thermoplastic elastomer extrusion, and/or a tungsten marker band and may assist a practitioner in visualizing the distal portion of the shaft 304. The marker band 326 may comprise, for example, approximately 60% barium sulphate. Although marker band 326 is shown at a distal end of the shaft 304, alternatively or in addition, one or more marker bands may be placed in any suitable location, including proximate one or more of the ports 316, proximate a portion of the shaft 304 configured to be adjacent to the IMD 302 when the IMD 302 is secured to the shaft 304, and/or any other suitable location as may assist a clinician in visualizing and positioning the kit 300 and implanting the IMD 302 within the vasculature of a patient.

In some examples, the proximal port 316b may be circumferentially spaced approximately 175-185 degrees about the shaft 304 from the distal port 316a. The circumferential spacing of ports 316 may allow for the IMD 302 to be more tightly secured to the shaft 304, e.g., by providing a greater linear distance between the ports 316, which may reduce the overall profile of the kit 300. In addition, the circumferential spacing of the ports 316 may reduce strain on the looped portions 312a and 312b.

FIGS. 3A and 3B show side cross-sectional and side profile views of the kit 300 assembled for positioning a distal end of the assembly at a target vascular location for implantation of the IMD 302. As shown, the tether 306 is pulled taught to firmly and securely attach the IMD 302 to the outer shaft 304 and to reduce the risk of contact damage from the fixation means contacting the walls of the vasculature before intended deployment of the IMD. For illustrative purposes, FIG. 3C shows a partially expanded view of the kit 300 with the tether 306 loosened, which may allow the looped portions 312a and 312b of the fixation assembly to expand. In practice, the tether 306 might be loose during assembly of the kit 300 and/or during deployment, for example, after retraction of the inner shaft 308 with respect to the outer shaft 304.

In some examples, the outer shaft 304 may be a braided stainless steel wire shaft. In some examples, the shaft 304 may include a jacket comprising a thermoplastic elastomer. The jacket may have decreasing durometer from the proximal end to distal end to increase the flexibility of the distal portion of the outer shaft 304. The outer diameter of the shaft 304 may be approximately 5.5-2.7 mm and an inner diameter of the outer shaft 304 may be approximately 0.5-1 mm.

In some examples, the ports 316 may be positioned in a distal portion of the shaft 304 that is approximately 70-80 mm long and that has a outer diameter of 1-1.5 mm. The distal portion may comprise for example, a polymer such as polymide, Pebax 63d-72d, or any other suitable material. The ports 316 may be positioned approximately 50-57 mm apart along the length of the distal portion. The distal portion of the outer shaft 304 may be bonded (e.g., by glue such as cyanoacrylate, ultraviolet cured, or a similar glue) to a distal end of a proximal portion of the outer shaft 304.

When the IMD 302 is secured to the outer shaft 304 by the tether 306 and the inner shaft 308, the outer diameter of the kit 300, including the IMD 302, may be less than approximately 4.35-4.73 mm and an introducer sheath of approximately 4.62-5.33 mm in diameter may be used with the kit 300.

In some examples, the inner shaft 308 may be a braided or nonbraided polyamide shaft. In some examples, the inner shaft 308 may have an outer diameter of approximately 0.76-0.86 mm and an inner diameter of approximately 0.508-0.66 mm and may be configured to receive the guidewire 322, e.g., may define a lumen there through.

In some examples, the guidewire 322 may be approximately 0.46-0.50 mm in diameter.

In some examples, the inner shaft 308 may include or be coupled to a handle mechanism to allow for a practitioner to manipulate the inner shaft 308 including, for example, advancing the inner shaft 308 with respect to the outer shaft 304 and through the looped portion 320a of the tether 306 to secure the IMD 302 to the outer shaft 304 or to retract the inner shaft 308 with respect to the outer shaft 304 to release the looped portion 320a of the tether and release the IMD 302 from the outer shaft 304. The handle may comprise an injection molded polymer and may include locking and unlocking functions to lock the inner shaft 308 in place and release the inner shaft 308 for movement by the practitioner, respectively. The handle may comprise a male luer threadably fixed to a proximal end of the outer shaft 304, which may facilitate delivery of the kit 300 via an over the wire method and/or a saline flush prior to introducing the kit 300 into the vasculature.

FIGS. 4A-4E are partial, schematic views of the kit 300 of FIGS. 3A-3C in various stages of use at an example treatment site within the vasculature 400 of a patient. FIG. 5 is a flow diagram illustrating an example method for intravascular implantation of an implantable medical device (IMD) 302 using the kit 300 of FIGS. 3A-3C.

Vasculature 400 may include walls 402 that define vascular lumen 404 and target location 408 may be a treatment site within vasculature 400. Target location 408 may be, for example, a location within a pulmonary artery in which IMD 302 is to be places.

Guidewire 322 may be inserted into vascular lumen 404 of a patient (FIG. 4A). The guidewire 322 may be advanced through vascular lumen 404 of vasculature 400 to position a distal end 406 of the guidewire 322 distal the target location 408 as determined by the clinician.

Figure 4B:
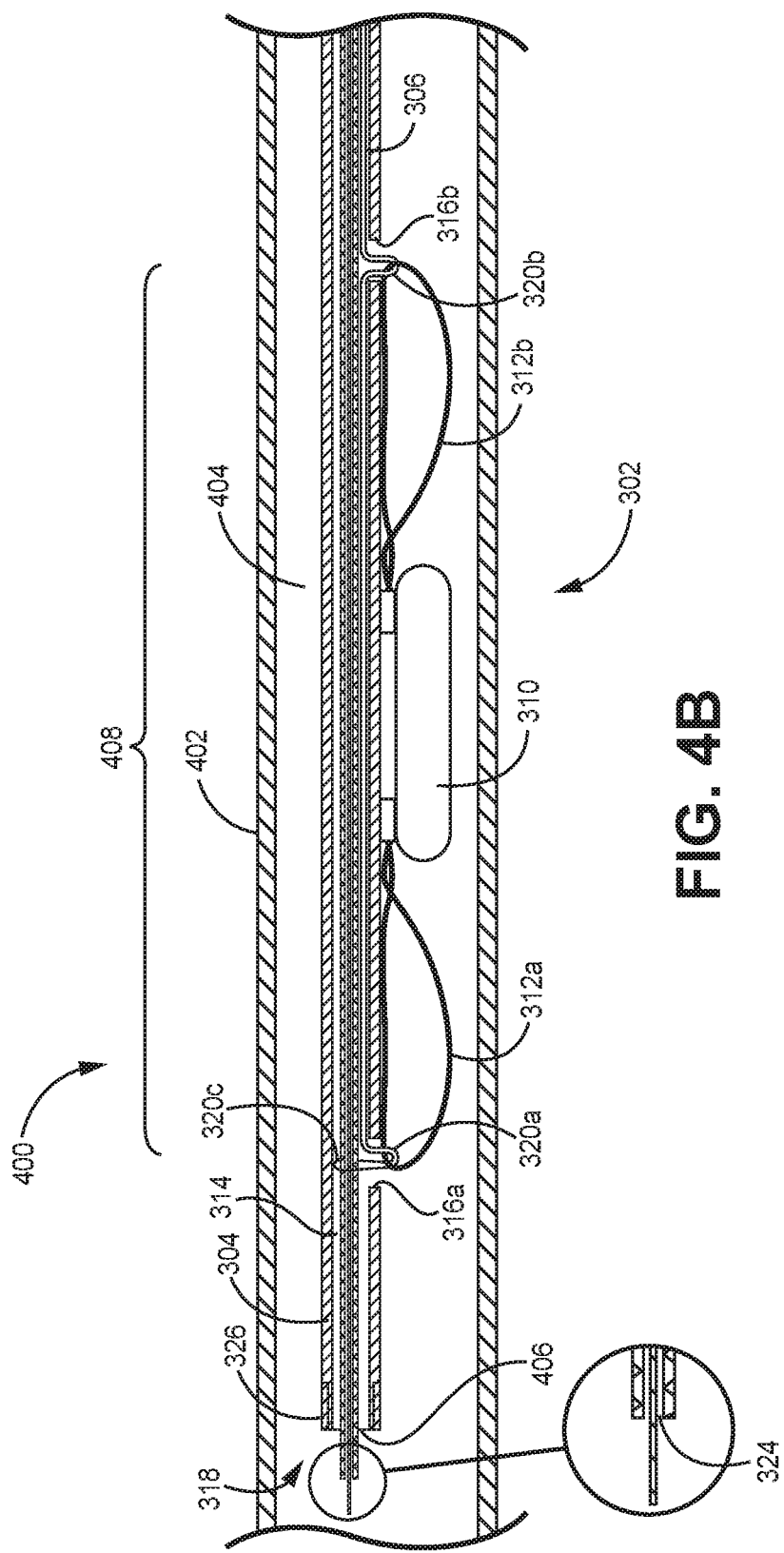
Figure 5:
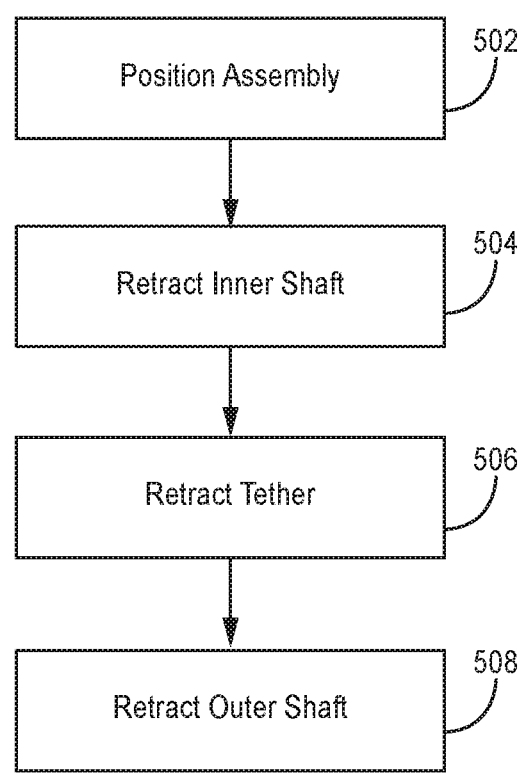
FIG. 5 is a flow diagram illustrating an example method for intravascular implantation of an implantable medical device (IMD) using the example kit of FIGS. 3A-3C.

A distal end 408 of the assembly 300 may be introduced over guidewire 322 and a distal portion of the kit 300 may be advanced and positioned at or proximate to the target location 408 (FIG. 4B and FIG. 5, Step 502). A radiopaque marker 326 and/or other radiopaque markers on the kit 300, may be used by the clinician to visualize the location of distal end of the kit 300, one or more of the ports 316, and/or a portion of the shaft adjacent to the IMD 302 to position the kit 300 and/or the IMD 302 with respect to target location 408. For example, radiopaque markers at the distal end of the outer shaft 304, proximate one or more of ports 316, and/or on a portion of the outer shaft 304 adjacent the IMD 302, may be helpful for positioning the IMD 302 at the target location 408.

The inner shaft 308 may be retracted relative to the outer shaft 304 such that it no longer passes through the looped portion 320a of the tether 306 (FIG. 4C and FIG. 5, Step 504). In some examples and as illustrated in FIG. 4C, the tether 306 may loosen and the looped portions 316 of the fixation assembly may expand or partially expand. In other examples, the tether 306 may be configured to remain taught after retraction of the inner shaft 308 so that the looped portions 316 of the fixation assembly may remain secured to the outer shaft until the tether 306 is retracted. In some examples, the guidewire 322 may be retracted before or at the same time that the inner shaft 308 is retracted.

Figure 4D:
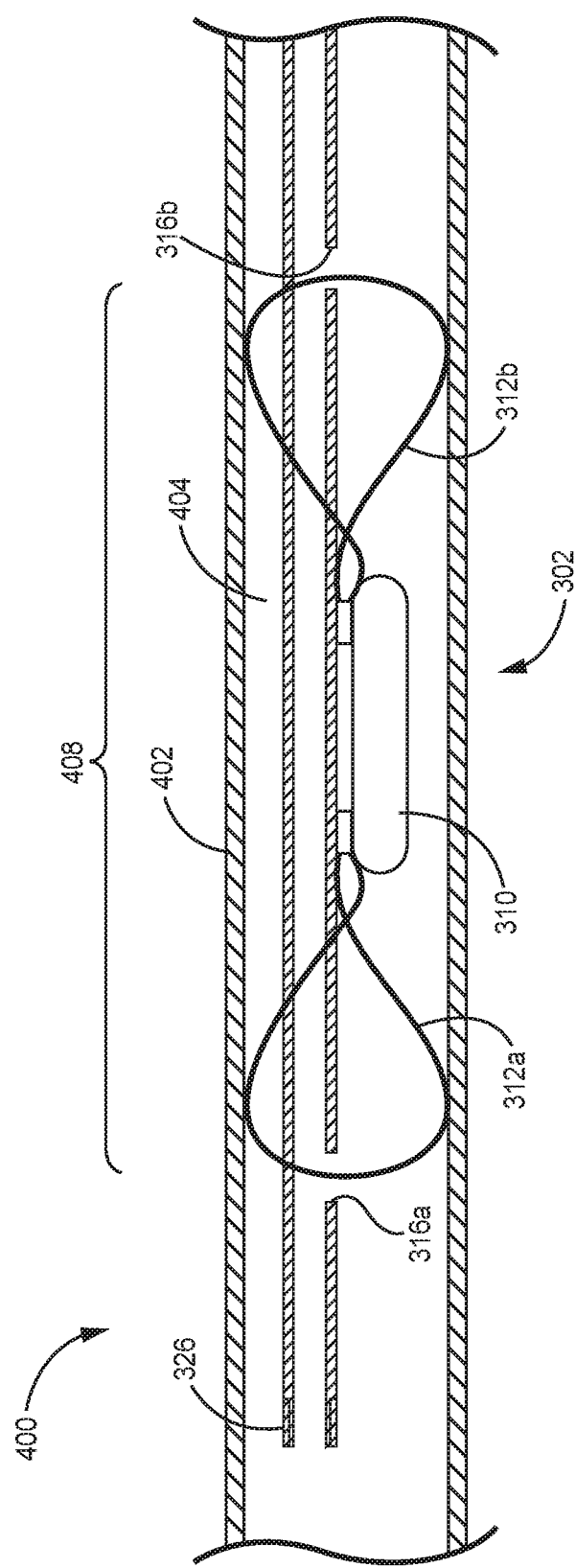

The tether 306 may be retracted relative to the outer shaft 304 such that the tether 306 no longer passes through the looped portions 316 of the fixation assembly (FIG. 4D and FIG. 5, Step 506). The looped portions 316 of the fixation assembly will fully expand, if they have not already done so, to the walls 402 of the vasculature 400 to secure the IMD 302 within the target location 408 of the vasculature.

Figure 4E:
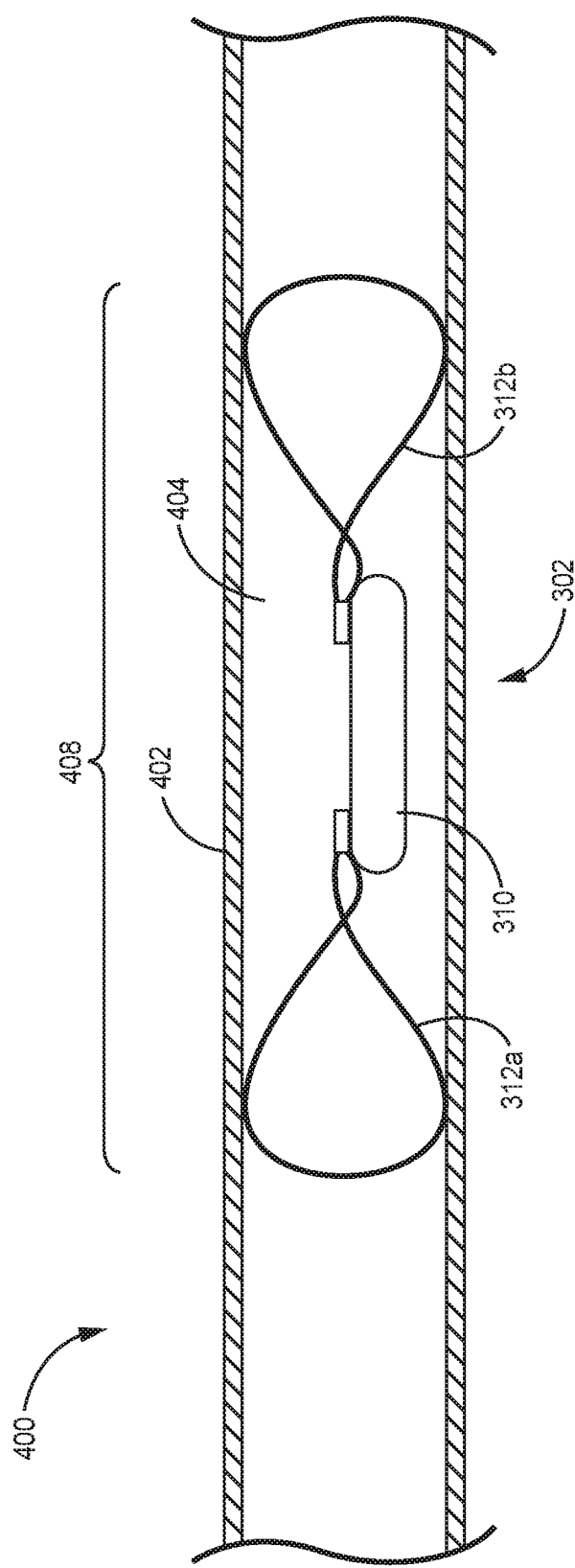

The outer shaft 304 may be removed from the vasculature 400 such that only the IMD 302 remains within the vasculature 400 (FIG. 4E and FIG. 5, Step 508).

Although an example of use of kit 300 has been described, any suitable modification may be made according to particular needs, including performing the steps in a different order and/or performing more, fewer steps, and/or different steps. For example, a practitioner may load the IMD onto the shaft. In some examples, the practitioner may use an unlock and/or lock function on a handle attached to the inner shaft 308 to load the IMD 302 onto the shaft 304, as described in further detail above with respect to FIGS. 3A-3C, and/or to retract the inner shaft 308 and/or the tether 306 to release the IMD 302 from the shaft. The method may further include closing an entry site into the vasculature 400 after implantation of the IMD 302 and removal of the other components of the kit 300.

Vasculature 400 may comprise, for example, the neurovasculature, peripheral vasculature, or cardiovasculature. Although a method of use is described for delivering an implantable medical device within a target location within a vasculature, kit 300 may be used for delivery of a device at any suitable location and for any suitable condition according to particular needs.

Various examples have been described. These and other examples are within the scope of the following claims.

What is claimed is:

1. A kit for intravascular implantation of an implantable medical device within a patient, the implantable medical device comprising a fixation element comprising a first looped portion and a second looped portion, the kit comprising:
   an elongated outer shaft defining a longitudinal lumen and defining a proximal port and a distal port on a side wall of the elongated outer shaft, the proximal port and the distal port in fluid communication with the lumen, the proximal port and the distal port located proximal a distal end of the elongated outer shaft, the elongated outer shaft sized to traverse a vasculature of the patient;
   a tether, wherein at least a first portion of the tether is configured to pass through the lumen of the elongated outer shaft, at least a second portion of the tether is configured to exit the lumen through the proximal port and pass through the first looped portion of the fixation element of the implantable medical device outside of the elongated outer shaft, at least a third portion of the tether is configured to define a looped portion of the tether, and at least a fourth portion of the tether is configured to exit the lumen through the distal port and pass through the second looped portion of the fixation element of the implantable medical device outside of the elongated outer shaft; and
   an elongated inner shaft, at least a portion of the elongated inner shaft configured to pass through the lumen of the elongated outer shaft and to pass through the looped portion of the tether to prevent removal of the tether from the elongated outer shaft when the portion of the elongated inner shaft passes through the looped portion of the tether.

2. The kit of claim 1, wherein the proximal port is circumferentially spaced approximately 180 degrees about the elongated outer shaft from the distal port.

3. The kit of claim 1, wherein the elongated inner shaft defines a guidewire lumen configured for passage of a guidewire.

4. The kit of claim 1, wherein a distal portion of the elongated outer shaft comprises a radiopaque marker.

5. The kit of claim 1, wherein the elongated inner shaft comprises braided polyamide.

6. The kit of claim 1, wherein the implantable medical device comprises a sensor configured to measure blood pressure.

7. A method for intravascular implantation of an implantable medical device within a patient, the method comprising:
- positioning a distal end of an assembly at a target vascular location for implantation of an implantable medical device, the assembly including:
  - an elongated outer shaft defining a longitudinal lumen and defining a proximal port and a distal port on a side wall of the elongated outer shaft, the proximal port and the distal port in fluid communication with the lumen, the proximal port and the distal port located proximal a distal end of the elongated outer shaft, the outer shaft sized to traverse a vasculature of the patient;
  - the implantable medical device comprising a fixation element comprising a first looped portion and a second looped portion;
  - a tether, wherein at least a first portion of the tether passes through the lumen of the outer shaft, at least a second portion of the tether exits the lumen through the proximal port and passes through the first looped portion of the fixation element of the implantable medical device outside of the elongated outer shaft, at least a third portion of the tether is configured to define a looped portion of the tether, and at least a fourth portion of the tether exits the lumen through the distal port and passes through the second looped portion of the fixation element of the implantable medical device outside of the elongated outer shaft; and
  - an elongated inner shaft, wherein at least a portion of the elongated inner shaft is configured to pass through the lumen of the elongated outer shaft and pass through the looped portion of the tether to prevent removal of the tether from the elongated outer shaft when the portion of the elongated inner shaft passes through the looped portion of the tether;
- retracting the elongated inner shaft relative to the elongated outer shaft; and
- retracting the tether relative to the elongated outer shaft.

8. The method of claim 7, wherein the proximal port is circumferentially spaced approximately 180 degrees about the elongated outer shaft from the distal port.

9. The method of claim 7, wherein the elongated inner shaft defines a guidewire lumen configured for passage of a guidewire, and the method further comprises positioning a distal end of the guidewire, wherein positioning the distal end of the assembly at the target vascular location comprise advancing the assembly over the guidewire.

10. The method of claim 7, wherein a distal portion of the elongated outer shaft comprises a radiopaque marker.

11. The method of claim 7, wherein the elongated inner shaft comprises braided polyamide.

12. A kit for intravascular implantation of an implantable medical device within a patient, the kit comprising:
- an elongated outer shaft defining a longitudinal lumen and defining a proximal port and a distal port on a side wall of the elongated outer shaft, the proximal port and the distal port in fluid communication with the lumen, the proximal port and the distal port located proximal a distal end of the elongated outer shaft, the elongated outer shaft sized to traverse a vasculature of the patient;
- the implantable medical device comprising a fixation element comprising a first looped portion and a second looped portion, wherein at least the first looped portion is an expandable looped portion;
- a tether, wherein at least a first portion of the tether is configured to pass through the lumen of the elongated outer shaft, at least a second portion of the tether is configured to exit the lumen through the proximal port and pass through the first looped portion of the fixation element of the implantable medical device outside of the elongated outer shaft, at least a third portion of the tether is configured to define a looped portion of the tether, and at least a fourth portion of the tether is configured to exit the lumen through the distal port and pass through the second looped portion of the fixation element of the implantable medical device outside of the elongated outer shaft; and
- an elongated inner shaft, at least a portion of the elongated inner shaft configured to pass through the lumen of the elongated outer shaft and to pass through the looped portion of the tether to prevent removal of the tether from the elongated outer shaft when the portion of the elongated inner shaft passes through the looped portion of the tether.

13. The kit of claim 12, wherein the proximal port is circumferentially spaced approximately 180 degrees about the elongated outer shaft from the distal port.

14. The kit of claim 12, wherein the elongated inner shaft defines a guidewire lumen configured for passage of a guidewire.

15. The kit of claim 12, wherein a distal portion of the elongated outer shaft comprises a radiopaque marker.

16. The kit of claim 12, wherein the elongated inner shaft comprises braided polyamide.

17. The kit of claim 12, wherein the implantable medical device comprises a sensor configured to measure blood pressure.

18. A kit for intravascular implantation of an implantable medical device within a patient, the implantable medical device comprising a fixation element comprising a first looped portion and a second looped portion, the kit comprising:
- an elongated outer shaft defining a longitudinal lumen, a proximal port in fluid communication with the lumen, and a distal port in fluid communication with the lumen, wherein each of the proximal port and the distal port are located proximal a distal end of the elongated outer shaft and defined on a side wall of the elongated outer shaft, wherein the elongated outer shaft is sized to traverse a vasculature of the patient;
- a tether, wherein at least a first portion of the tether is configured to pass through the lumen of the elongated outer shaft, at least a second portion of the tether is configured to exit the lumen through the proximal port and pass through the first looped portion of the fixation element of the implantable medical device outside of the elongated outer shaft, at least a third portion of the tether is configured to exit the lumen through the distal port and pass through the second looped portion of the fixation element of the implantable medical device outside of the elongated outer shaft, and at least a fourth portion of the tether defines a looped portion of the tether; and
- an elongated inner shaft, at least a portion of the elongated inner shaft configured to pass through the lumen of the elongated outer shaft and to pass through the looped portion of the tether to prevent removal of the tether from the elongated outer shaft when the portion of the elongated inner shaft passes through the looped portion of the tether.

19. A kit for intravascular implantation of an implantable medical device within a patient, the implantable medical device comprising a fixation element comprising a first looped portion and a second looped portion, the kit comprising:

an elongated outer shaft defining a longitudinal lumen, a proximal port in fluid communication with the lumen, and a distal port in fluid communication with the lumen, wherein each of the proximal port and the distal port are located proximal a distal end of the elongated outer shaft and defined on a side wall of the elongated outer shaft, wherein the proximal port is circumferentially spaced approximately 180 degrees about the elongated outer shaft from the distal port, wherein the elongated outer shaft is sized to traverse a vasculature of the patient, wherein a distal portion of the elongated outer shaft comprises a radiopaque marker;

a tether, wherein at least a first portion of the tether is configured to pass through the lumen of the outer shaft, at least a second portion of the tether is configured to exit the lumen through the proximal port and pass through the first looped portion of the fixation element of the implantable medical device outside of the elongated outer shaft, at least a third portion of the tether is configured to exit the lumen through the distal port and pass through the second looped portion of the fixation element of the implantable medical device outside of the elongated outer shaft, and at least a fourth portion of the tether defines a looped portion of the tether; and an elongated inner shaft, at least a portion of the elongated inner shaft configured to pass through the lumen of the elongated outer shaft and to pass through the looped portion of the tether to prevent removal of the tether from the elongated outer shaft when the portion of the elongated inner shaft passes through the looped portion of the tether.

\* \* \* \* \*